(12) United States Patent
Wang et al.

(10) Patent No.: US 7,474,397 B2
(45) Date of Patent: Jan. 6, 2009

(54) RAMAN AND HYPER-RAMAN EXCITATION USING SUPERLENSING

(75) Inventors: Shih-Yuan Wang, Palo Alto, CA (US); Zhiyong Li, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 48 days.

(21) Appl. No.: 11/413,377

(22) Filed: Apr. 28, 2006

(65) Prior Publication Data

US 2007/0252980 A1 Nov. 1, 2007

(51) Int. Cl.
*G01J 3/44* (2006.01)
(52) U.S. Cl. ...................................... 356/301
(58) Field of Classification Search ................ 356/301, 356/80; 355/80
See application file for complete search history.

(56) References Cited

U.S. PATENT DOCUMENTS

| | | | | |
|---|---|---|---|---|
| 7,242,470 | B2 * | 7/2007 | Cullum et al. | 356/301 |
| 2002/0123050 | A1 * | 9/2002 | Poponin | 435/6 |
| 2003/0227415 | A1 | 12/2003 | Joannopoulos et al. | |
| 2007/0159617 | A1 * | 7/2007 | Mackey | 355/80 |

OTHER PUBLICATIONS

Berrier, A., et al., "Negative Refraction at Infrared Wavelengths in a Two-DImensional Photonic Crystal," Physical Review Letters, vol. 93, No. 7, pp. 073902-1 through 073902-4, Aug. 13, 2004.

Blaikie, Richard J., et al., "Imaging through planar silver lenses in the optical near field," J. Opt. A: Pure Appl. Opt., vol. 7, pp. S176-S183, 2005.

Fang, Nicholas, et al., "Sub-DIffraction-Limited Optical Imaging with a Silver Superlens," Science, vol. 308, pp. 534-537. Apr. 22, 2005.

Lagarkov, A.N., et al., "Near-Perfect Imaging in a Focusing System Based on a Left-Handed-Material Plate," Physical Review Letters. vol. 92, No. 7, pp. 077401-1 through 077401-4, Feb. 20, 2004.

Linden, Stepfan, et al., "Magnetic Response of Metamaterials at 100 Terahertz," Science, vol. 306, pp. 1351-1353, Nov. 19, 2004.

Liu, Liu, et al., "Near-field optical storage system using a solid immersion lens with a left-handed material stab," Optics Express, vol. 12, No. 20, pp. 4835-4840, Oct. 4, 2004.

(Continued)

*Primary Examiner*—Kara E Geisel
*Assistant Examiner*—Abdullahi Nur (57) ABSTRACT

Raman-enhancing structures include a layer of dielectric material, a superlens configured to focus electromagnetic radiation having a wavelength greater than about 100 nanometers to a two-dimensional focal area having linear dimensions less than about 100 nanometers on a surface of the layer of dielectric material, and at least two nanoparticles comprising a Raman-enhancing material disposed proximate the focal area. Additional Raman-enhancing structures include a layer of dielectric material, a layer of conductive material, and at least two nanoparticles comprising a Raman-enhancing material disposed on a second, opposite surface of the layer of dielectric material. The layer of conductive material has a plurality of apertures therethrough that are arranged in a two-dimensional array. Methods for conducting Raman spectroscopy are performed using such structures and systems.

21 Claims, 6 Drawing Sheets

OTHER PUBLICATIONS

Parazzoli, C.G., et al., "Experimental Verification and Simulation of Negative Index of Refraction Using Snell's Law," Physical Review Letters, vol. 90, No. 10, pp. 107401-1 through 107401-4, Mar. 14, 2003.

Pendry, J.B., "Negative Refraction Makes a Perfect Lens," Physical Review Letters, vol. 85, No. 18, pp. 3966-3969, Oct. 30, 2000.

Prodan, E., "A Hybridization Model for the Plasmon Response of Complex Nanostructures," Science, vol. 302, pp. 419-422, Oct. 17, 2003.

Qui, Min, et al., "Wave Propagation Through a Photonic Crystal in a Negative Phase Refractive-Index Region," IEEE Journal of Selected Topics in Quantum Electronics, vol. 9, No. 1, pp. 106-110, Jan./Feb. 2003.

Ramakrishna, S. Anantha, et al., "Removal of absorption and increase in resolution in a near-field lens via optical gain," Physical Review B, vol. 67, pp. 201101-1 through 201101-4, 2003.

Srituravanich, Werayut, et al., "Plasmonic Nanolithography," Nano Lett., vol. 4, No. 6, pp. 1085-1088, 2004.

Srituravanich, W., et al., "Sub-100 nm lithography using ultrashort wavelength of surface plasmons," J. Vac. Sci. Technol. B, vol. 22, No. 6, pp. 3475-3478, Nov./Dec. 2004.

Urzhumov, Yaroslav, "Superlensing with 2D subwavelength photonic crystals," Physics Dept., Univ. of Texas at Austin, pp. 1-34, Mar. 29, 2005.

Wang, X., et al., "Unrestricted superlensing in a triangular two-dimensional photonic crystal," Optics Express, vol. 12, No. 13, pp. 2919-2924, Jun. 28, 2004.

* cited by examiner

RAMAN AND HYPER-RAMAN EXCITATION USING SUPERLENSING

FIELD OF THE INVENTION

The present invention relates to Raman spectroscopy. More particularly, the invention relates to Raman-enhancing structures configured to enhance the intensity of Raman scattered radiation that is scattered by an analyte, Raman spectroscopy systems including such Raman-enhancing structures, and methods for performing Raman spectroscopy using such Raman-enhancing structures.

BACKGROUND OF THE INVENTION

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. In Raman spectroscopy, the wavelength of the incident radiation typically is varied over a range of wavelengths within or near the visible region of the electromagnetic spectrum. A majority of the photons of the incident radiation are elastically scattered by the analyte. In other words, the scattered photons have the same energy, and thus the same wavelength, as the incident photons. However, a very small fraction of the photons are inelastically scattered by the analyte. Typically, only about 1 in $10^7$ of the incident photons are inelastically scattered by the analyte. These inelastically scattered photons have a different wavelength than the incident photons. This inelastic scattering of photons is termed "Raman scattering". The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons as evidenced by their wavelength, frequency, or wave number, and the number of the Raman scattered photons as evidenced by the intensity of the Raman scattered radiation. The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes including identification of an unknown analyte, or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface-enhanced Raman spectroscopy (SERS) is a technique that allows for enhancement of the intensity of the Raman scattered radiation relative to conventional Raman spectroscopy. In SERS, the analyte molecules typically are adsorbed onto or placed adjacent to what is often referred to as a SERS-active structure. SERS-active structures typically include a metal surface or structure. Interactions between the analyte and the metal surface may cause an increase in the intensity of the Raman scattered radiation. The mechanism by which the intensity of the Raman scattered radiation is enhanced is not precisely understood.

Several types of metallic structures have been employed in SERS techniques to enhance the intensity of Raman scattered radiation that is scattered by analyte molecules adjacent thereto. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface made from gold or silver can enhance the Raman scattering intensity by factors of between $10^3$ and $10^6$.

Raman spectroscopy recently has been performed employing randomly oriented nanoparticles, such as nanometer scale needles, particles, and wires, as opposed to a simple roughened metallic surface. The process of performing Raman spectroscopy utilizing structures comprising nanoparticles to enhance the intensity of Raman scattered radiation will be referred to herein as nano-enhanced Raman spectroscopy (NERS). The intensity of the Raman scattered photons from a molecule adsorbed on such a nanostructure can be increased by factors as high as $10^{16}$. At this level of sensitivity, NERS has been used to detect single molecules. Detecting single molecules with high sensitivity and molecular specificity is of great interest in the fields of chemistry, biology, medicine, pharmacology, and environmental science.

Hyper-Raman spectroscopy is another Raman spectroscopy technique that involves detecting the shift from the second order harmonic of the excitation frequency. The hyper-Raman scattered radiation is Raman-shifted relative to integer multiples of the frequency of the incident electromagnetic radiation. Hyper-Raman scattered radiation can provide information about the analyte that cannot be obtained from normal Raman spectroscopy. The intensity of the hyper-Raman scattered radiation, however, is even less than the intensity of the Raman scattered radiation. As a result, hyper-Raman spectroscopy typically is performed using SERS-active or NERS-active structures.

One limitation inherent in heretofore known Raman spectroscopy systems is the inability to focus the incident electromagnetic radiation to a "spot size" having linear measurements less than about one wavelength of the electromagnetic radiation due to the diffraction limit. As Raman spectroscopy typically is performed using incident electromagnetic radiation in or near the visible region of the electromagnetic spectrum, the incident electromagnetic radiation generally cannot be focused to a spot size smaller than about 100 nanometers in diameter. This inability to provide a relatively smaller spot size precludes performing Raman spectroscopy on smaller, more precise regions of an analyte. It is desirable to provide ever smaller spot sizes, which theoretically could be used to conduct Raman spectroscopy on a particular portion of a molecule, such as, individual nucleotides of a DNA molecule or particular amino acids or peptides of a protein. Therefore, it is desirable to provide Raman spectroscopy systems configured to emit incident electromagnetic radiation to ever smaller spot sizes.

BRIEF SUMMARY OF THE INVENTION

In one aspect, the present invention includes Raman-enhancing structures that include a substantially planar layer of dielectric material, a superlens, and at least two nanoparticles comprising a Raman-enhancing material. The layer of dielectric material has a first surface and a second, opposite surface. The superlens is configured to focus electromagnetic radiation having a wavelength of greater than about 100 nanometers to a two-dimensional focal area having linear dimensions less than about 100 nanometers on one of the first and second surfaces of the layer of dielectric material. The at least two nanoparticles are disposed proximate the two-dimensional focal area.

In another aspect, the present invention includes Raman-enhancing structures that include a substantially planar layer of dielectric material, a substantially planar layer of conductive material having a thickness of less than about 100 nanometers, and at least two nanoparticles comprising a Raman-enhancing material. The layer of dielectric material has a first surface and a second, opposite surface. The layer of conductive material is disposed on the first surface of the layer of dielectric material. Furthermore, the layer of conductive material includes a plurality of apertures extending therethrough. The apertures are arranged in a two-dimensional array. The at least two nanoparticles are disposed on the second surface of the layer of dielectric material.

In another aspect, the present invention includes methods for performing Raman spectroscopy. The methods include generating electromagnetic radiation having a selected wavelength greater than about 100 nanometers, focusing at least a portion of the electromagnetic radiation to a two-dimensional focal area having linear dimensions less than about 100 nanometers, providing an analyte proximate the two-dimensional focal area, subjecting the analyte to the focused electromagnetic radiation, and detecting Raman scattered radiation that is scattered by the analyte.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention relates to Raman spectroscopy. More particularly, the invention relates to Raman-enhancing structures configured to enhance the intensity of Raman scattered radiation that is scattered by an analyte, Raman spectroscopy systems including such Raman-enhancing structures, and methods for performing Raman spectroscopy using such Raman-enhancing structures.

The term "nanostructure" as used herein means a structure that includes at least one nanoparticle. The term "nanoparticle" as used herein means a particle of any shape having cross-sectional dimensions of less than about 100 nanometers. Examples of nanoparticles include, but are not limited to, nanodots, nanowires, nanolines, nanocolumns, and nanospheres. The term "analyte" as used herein means any molecule, molecules, material, substance, or matter that is to be analyzed by Raman spectroscopy.

The term "Raman-enhancing material" as used herein means a material that, when formed into appropriate geometries or configurations, is capable of increasing the number of Raman scattered photons that are scattered by an analyte when the analyte is located proximate to that material, and the analyte and material are subjected to electromagnetic radiation. Raman-enhancing materials typically include, but are not limited to, highly conductive metals such as silver, gold, and copper.

The term "superlens" as used herein means any lens or structure that is capable of focusing electromagnetic radiation to a two-dimensional focal area having linear dimensions that are less than the wavelength of the electromagnetic radiation. The term "two-dimensional focal area" as used herein means a region on a surface at which the intensity of electromagnetic radiation is higher than in immediately surrounding regions. The term "focus" as used herein means to bring electromagnetic radiation from a region of relatively lower intensity to a region of relatively higher intensity.

The illustrations presented herein are not meant to be actual views of any particular Raman-enhancing structure or Raman spectroscopy system, but are merely idealized representations which are employed to describe the present invention. Additionally, elements common between figures may retain the same numerical designation.

Figure 1:
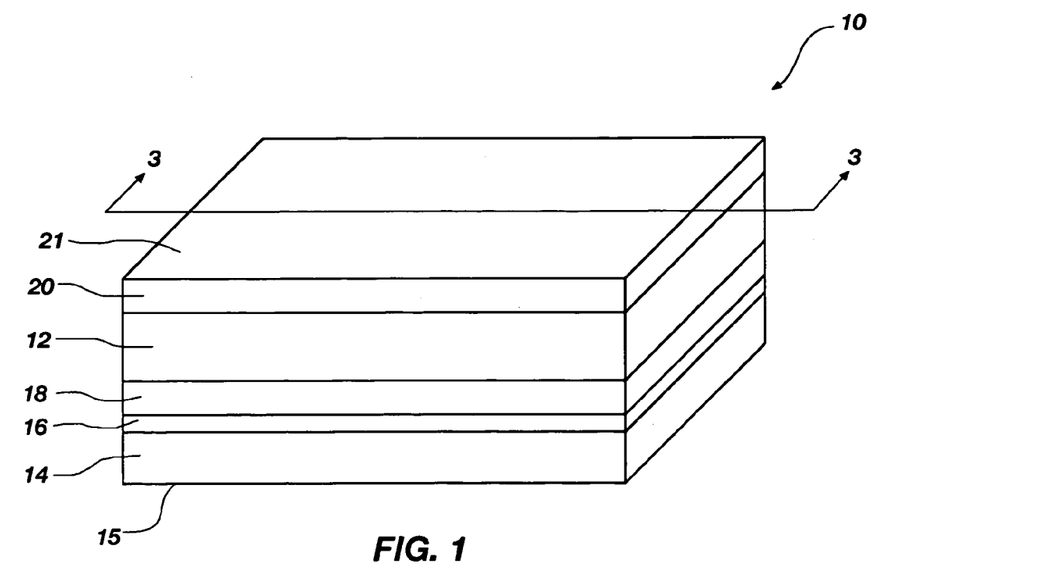
FIG. 1 is a perspective view of an exemplary Raman-enhancing structure that embodies teachings of the present invention.

An exemplary Raman-enhancing structure 10 that embodies teachings of the present invention is shown in FIG. 1. The Raman-enhancing structure 10 includes a superlens 12, which will be described in detail herein below. The Raman-enhancing structure 10 also may include a base substrate 14, a screen layer 16, a first layer of dielectric material 18, and a second layer of dielectric material 20. Each of these layers may be substantially planar. The superlens 12 is configured to focus electromagnetic radiation (not shown in FIG. 1) passing through the superlens 12 to a two-dimensional focal area (not shown in FIG. 1) having linear dimensions of less than about 100 nanometers. For example, the superlens 12 may be configured to focus at least a portion of electromagnetic radiation that is incident on an exposed surface 15 of the base substrate 14 to a two-dimensional focal area on an exposed surface 21 of the second layer of dielectric material 20. The exposed surface 12 of the base substrate 14 and the exposed surface 21 of the second layer of dielectric material 20 may be disposed on opposite sides of the Raman-enhancing structure 10, as shown in FIG. 1.

The base substrate 14, the first layer of dielectric material 18, and the second layer of dielectric material 20 each may be transparent to electromagnetic radiation over a range of wavelengths at which Raman spectroscopy may be performed. The screen layer 16 may be opaque to these wavelengths of electromagnetic radiation.

Figure 2:
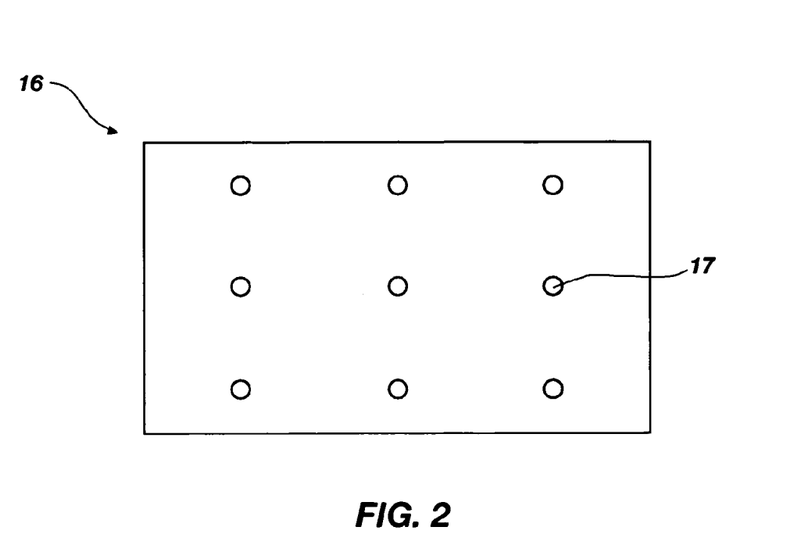
FIG. 2 is a plan view of an element of the Raman-enhancing structure shown in FIG. 1.

FIG. 2 is a plan view of the screen layer 16 of the Raman-enhancing structure 10 shown in FIG. 1. As seen in FIG. 2, at least one aperture 17 may be provided through the screen layer 16. The aperture 17 may have cross-sectional dimensions of less than about 100 nanometers. For example, the aperture 17 may be configured as a cylindrical hole passing through the screen layer 16 having a diameter of less than about 100 nanometers. Alternatively, the aperture 17 may be configured to have other shapes. As will be described below, the size and shape of the at least one aperture 17 in the screen layer 16 may define the size and shape of the two-dimensional focal area of the superlens 12.

In one particular embodiment of the present invention, the base substrate 14 may be formed from quartz, and the first layer of dielectric material 18 and the second layer of dielectric material 20 each may be formed from polymethyl methacrylate (PMMA). It may be desirable to ensure that the material of the first layer of dielectric material 18 has a dielectric constant similar to the dielectric constant of the material of the second layer of dielectric material 20. Therefore, the first layer of dielectric material 18 and the second layer of dielectric material 20 may be formed from the same material. The screen layer 16 may be formed from, for example, chrome. If the screen layer 16 is formed from a metal, the metal should not exhibit significant surface plasmon resonance over the range of wavelengths at which Raman spectroscopy is to be performed.

In one particular embodiment of the invention, the screen layer 16 may have a thickness of about 50 nanometers, the first layer of dielectric material 18 may have a thickness of about 40 nanometers, the superlens 12 may have a thickness of about 35 nanometers, and the second layer of dielectric material 20 may have a thickness in a range from about 10 nanometers to about 100 nanometers. Furthermore, the surfaces of both the superlens 12 and the first layer of dielectric material 18 may be extremely smooth, and may have a surface root mean square modulation below about 1 nanometer.

Figure 3:
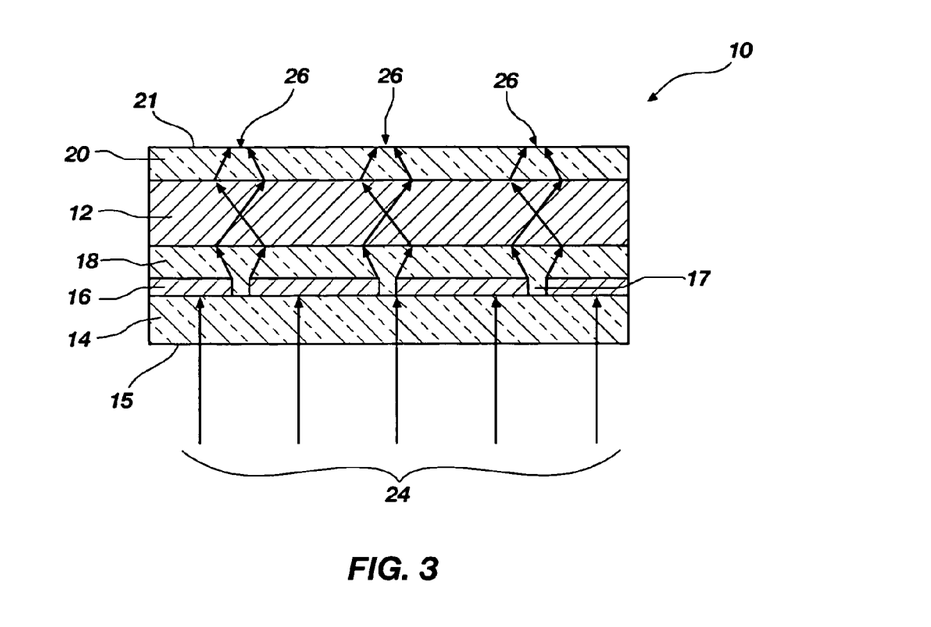
FIG. 3 is a cross-sectional view of the Raman-enhancing structure shown in FIG. 1 taken along section line 3-3 shown therein, illustrating operation of the Raman-enhancing structure.

FIG. 3 is a cross-sectional view of the Raman-enhancing structure 10 shown in FIG. 1, enhanced to illustrate operation of the Raman-enhancing structure 10. As seen in FIG. 3, the exposed surface 15 of the base substrate 14 may be irradiated with electromagnetic radiation 24. The electromagnetic radiation may have a wavelength of, for example, 365 nanometers. As the base substrate 14 is transparent to the electromagnetic radiation 24, the radiation 24 may be transmitted through the base substrate 14 and may impinge on a surface of the screen layer 16. As the screen layer 16 is opaque to the electromagnetic radiation 24, the electromagnetic radiation 24 may pass through the screen layer 16 only at the apertures 17 extending therethrough. As the electromagnetic radiation 24 passes through the apertures 17 in the screen layer 16, the electromagnetic radiation 24 may be diffracted and refracted.

The superlens 12 may be configured to exhibit a negative index of refraction. The path of the electromagnetic radiation 24 between the screen layer 16 and the exposed surface 21 of the second layer of dielectric material may be described by Snell's law, considering the negative index of refraction of the superlens. As seen in FIG. 3, the electromagnetic radiation 24 may be focused by the superlens to a two-dimensional focal area 26 on the exposed surface 21 of the second layer of dielectric material 20. The two-dimensional focal area 26 may have a size and shape substantially similar to the size and shape of a cross-section of the apertures 17 passing through the screen layer 16. Furthermore, if the electromagnetic radiation 24 includes evanescent waves as the electromagnetic radiation 24 passes through the apertures 17, these evanescent waves may be amplified as they pass through the superlens 12, and may be present at the two-dimensional focal area 26.

The area of the two-dimensional focal area 26 may be substantially smaller than could be achieved without use of the superlens 12. In this manner, the Raman-enhancing structure 10 may be used to provide incident electromagnetic radiation having a "spot size" that is much smaller than has previously been achieved in Raman spectroscopy. For example, this may allow Raman spectroscopy to be performed at very precise positions on an analyte. Furthermore, because the analyte may be subjected to the evanescent electromagnetic radiation in addition to far-field electromagnetic radiation, the intensity of the incident electromagnetic radiation 24 at the two-dimensional focal area 26 may be higher than could otherwise be attained, which may enhance the intensity of Raman scattered radiation scattered by an analyte.

In order to exhibit a negative index of refraction the superlens 12 may be constructed of a highly conductive metal that exhibits surface plasmon resonance over the range of wavelengths of electromagnetic radiation at which Raman spectroscopy is to be performed. For example, the superlens 12 may include Ag, Au, or Cu. Several configurations of superlenses have been researched and reported in the academic literature, many of which may be adapted and used in conjunction with the teachings herein to provide Raman-enhancing structures that embody teachings of the present invention.

To perform Raman spectroscopy using the Raman-enhancing structure 10, an analyte (not shown) may be provided at one or more of the two-dimensional focal areas 26 on the exposed surface 21 of the second layer of dielectric material 20. Electromagnetic radiation 24 may be generated at a selected wavelength. The exposed surface 15 of the base substrate 14 may be irradiated with the electromagnetic radiation 24. The screen layer 16 may provide at least one nanometer scale aperture 17 through which the electromagnetic radiation 24 is allowed to pass. The superlens 12 may focus the electromagnetic radiation passing through the at least one aperture 17 of the screen layer 16 to the one or more two-dimensional focal areas 26 on the exposed surface 21 of the second layer of dielectric material 20. The analyte may be subjected to this focused electromagnetic radiation 24. Raman scattered radiation may be scattered by the analyte, and this Raman scattered radiation may be detected by a detector (not shown in FIG. 3).

Figure 4:
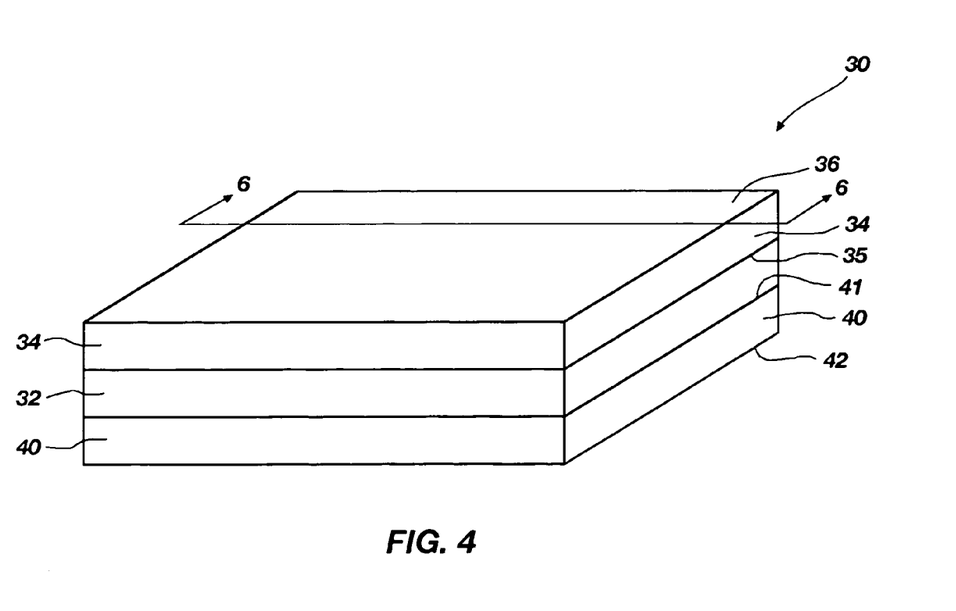
FIG. 4 is a perspective view of another exemplary Raman-enhancing structure that embodies teachings of the present invention.

Another exemplary Raman-enhancing structure 30 that embodies teachings of the present invention is shown in FIG. 4. The Raman-enhancing structure 30 includes a substantially planar layer of conductive material 32, and a substantially planar first layer of dielectric material 34. The Raman-enhancing structure 30 also may include a substantially planar second layer of dielectric material 40. The layer of conductive material 32 may be disposed on a surface of at least one of the first layer of dielectric material 34 and second layer of dielectric material 40. In one particular embodiment of the invention, the layer of conductive material 32 may be disposed between the first layer of dielectric material 34 and the second layer of dielectric material 40, as shown in FIG. 4.

The first layer of dielectric material 34 may include a first planar surface 35 disposed on a first side thereof and a second planar surface 36 disposed on a second, opposite side thereof. Similarly, the second layer of dielectric material 40 may include a first planar surface 41 disposed on a first side thereof and a second planar surface 42 disposed on a second, opposite side thereof. As shown in FIG. 4, the layer of conductive material 32 may be joined to the first planar surface 35 of the first layer of dielectric material 34 and to the first planar surface 41 of the second layer of dielectric material 40. The second planar surface 36 of the first dielectric material 34 may provide a first exposed surface of the Raman-enhancing structure 30, and the second planar surface 42 of the second layer of dielectric material may provide a second, opposite exposed surface of the Raman-enhancing structure 30.

The first layer of dielectric material 34 and the second layer of dielectric material 40 each may be transparent to electromagnetic radiation over a range of wavelengths at which Raman spectroscopy may be performed. For example, the first layer of dielectric material 34 and the second layer of dielectric material 40 each may be formed from quartz or a polymer material such as PMMA. Alternatively, the first layer of dielectric material 34 may be formed from quartz and the second layer of dielectric material 40 may be formed from PMMA. Many other materials may be transparent to electromagnetic radiation at the wavelengths of interest and may also be used. It may be desirable, however, to form the first layer of dielectric material 34 and the second layer of dielectric material 40 from materials that have similar refractive indices.

The layer of conductive material 32 may be formed from a highly conductive metal that exhibits surface plasmon resonance over a range of wavelengths of electromagnetic radiation at which Raman spectroscopy is to be performed. For example, the layer of conductive material 32 may include Ag, Au, or Cu.

Figure 5:
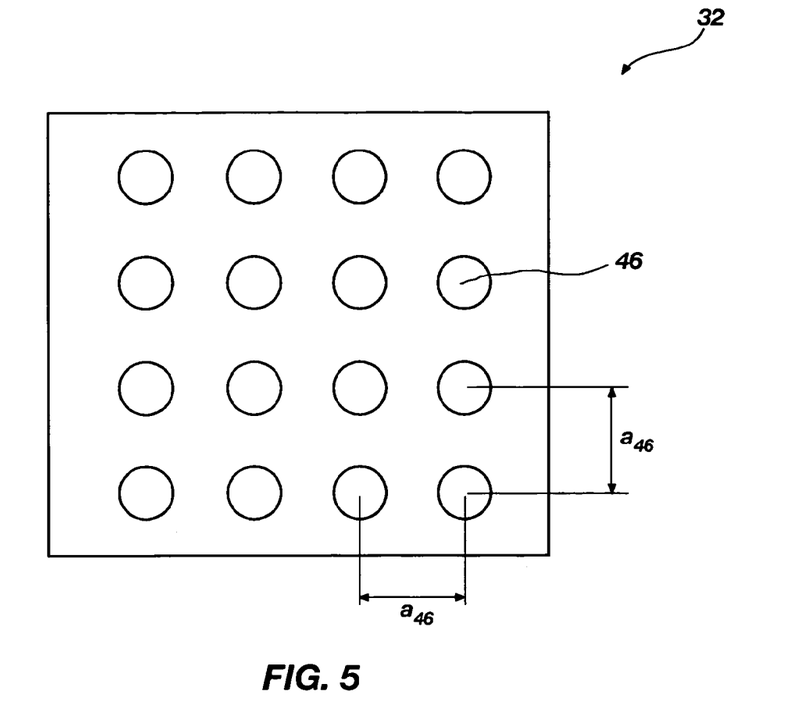
FIG. 5 is a plan view of an element of the Raman-enhancing structure shown in FIG. 4.

Referring to FIG. 5, the layer of conductive material 32 may have a plurality of apertures 46 extending therethrough. The plurality of apertures 46 may be arranged in a two-dimensional array, such as a rectangular array as shown in FIG. 5. Each aperture 46 may have cross-sectional dimensions of less than about 100 nanometers. Each aperture 46 of the plurality of apertures 46 may be substantially cylindrical having a longitudinal axis extending in a direction substantially perpendicular to the substantially planar layer of conductive material 32. The two-dimensional array of apertures 46 may have a period $a_{46}$ defined as the distance between the longitudinal axes of adjacent apertures 46 in the array. The period $a_{46}$ may be in a range from about 30 nanometers to about 1 micron. In one particular embodiment of the invention, each aperture 46 may have a diameter of about 40 nanometers, and the period $a_{46}$ of the two-dimensional array of apertures 46 may be about 170 nanometers. It should be understood that the layer of conductive material 32 is not shown to scale in FIG. 5, and that the length and width of the layer of conductive material 32 may be sufficiently large so as to include several hundred or even thousands of apertures 46 therein. In other words, the length and width of the layer of conductive material 32 (and the Raman-enhancing structure 30 shown in FIG. 4) need not be on the order of four apertures 46, as might be inferred from FIG. 5.

The layer of conductive material 32 may have a thickness of less than about 100 nanometers. The first layer of dielectric material 34 may have a thickness in a range from about 10 to about 100 nanometers. The thickness of the second layer of dielectric material 40 may not be particularly important.

Figure 6:
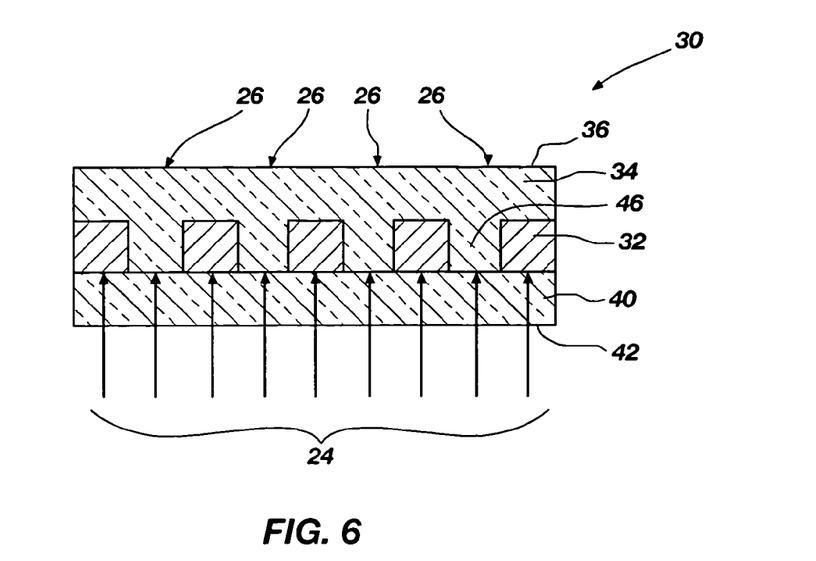
FIG. 6 is a cross-sectional view of the Raman-enhancing structure shown in FIG. 4 taken along section line 6-6 shown therein, illustrating operation of the Raman-enhancing structure.

The layer of conductive material 32 may be used to provide a plurality of two-dimensional focal areas 26 on the second planar surface 36 of the first layer of dielectric material 34, as shown in FIG. 6. Snell's law may not completely describe the behavior of the electromagnetic radiation 24 between the layer of conductive material 32 and the second planar surface 36 of the first layer of dielectric material 34. This may be due, at least in part, to complex interactions between the electromagnetic radiation 24 and surface plasmons on the surfaces of the layer of conductive material 32.

In this manner, the Raman-enhancing structure 30 may be used to provide a "spot size" much smaller than has been heretofore achieved in Raman spectroscopy. This may allow Raman spectroscopy to be performed at very precise positions on an analyte. Furthermore, an analyte may be subjected to relatively higher intensity of incident electromagnetic radiation 24 at the two-dimensional focal areas 26, which may enhance the intensity of Raman scattered radiation scattered by the analyte.

To perform Raman spectroscopy using the Raman-enhancing structure 30, an analyte (not shown) may be provided at one or more of the two-dimensional focal areas 26 on the second planar surface 36 of the second layer of dielectric material 34. Electromagnetic radiation 24 may be generated at a selected wavelength. The second planar surface 42 of the second layer of dielectric material 40 may be irradiated with the electromagnetic radiation 24. The layer of conductive material 32 may "focus" the electromagnetic radiation to the one or more two-dimensional focal areas 26 on the second planar surface 36 of the second layer of dielectric material 34. The analyte may be subjected to this focused electromagnetic radiation 24. Raman scattered radiation may be scattered by the analyte, and this Raman scattered radiation may be detected by a detector (not shown in FIG. 6).

The Raman-enhancing structure 10 shown in FIG. 1 and the Raman-enhancing structure 30 shown in FIG. 4 each may be formed using conventional epitaxial and lithographic methods known in the art of microdevice and nanodevice fabrication. For example, to fabricate the Raman-enhancing structure 30 shown in FIG. 4, a commercially available quartz substrate may be provided and used to form the second layer of dielectric material 40. The layer of conductive material 32 may be provided on the first planar surface 41 of the second layer of dielectric material 40 by, for example, physical vapor deposition. The apertures 46 may be formed in the layer of conductive material 32 by, for example, focused ion beam lithography. A layer of PMMA then may be spun onto the surface of the layer of conductive material 32 to provide the first layer of dielectric material 34. Many other methods than those discussed herein are known in the art and may be used to form the Raman-enhancing structures described herein.

Figure 7:
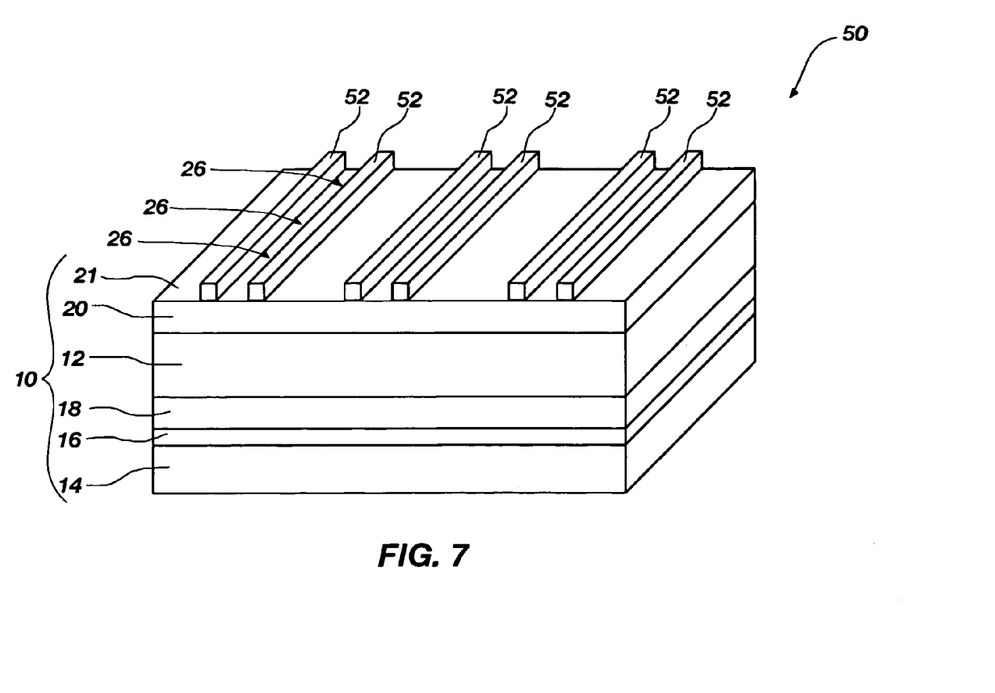
FIG. 7 is a perspective view of another exemplary Raman-enhancing structure that embodies teachings of the present invention.

FIG. 7 illustrates another exemplary Raman-enhancing structure 50 that embodies teachings of the present invention. The Raman-enhancing structure 50 is substantially similar to the Raman-enhancing structure 10 shown in FIG. 1. The Raman-enhancing structure 50 shown in FIG. 7, however, further includes at least two nanoparticles 52 formed from a Raman-enhancing material that are disposed proximate at least one of the two-dimensional focal areas 26 on the exposed surface 21 of the second layer of dielectric material 20. Only three of the two-dimensional focal areas 26 are labeled in FIG. 7. The nanoparticles 52 may be configured as, for example, nanolines of one of Au, Ag, and Cu. Any other configuration of nanoparticle also may be used. Each two-dimensional focal area 26 may be disposed between two nanoparticles 52 comprising Raman-enhancing material. The nanoparticles 52 comprising a Raman-enhancing material may further enhance the intensity of Raman scattered radiation that is scattered by an analyte when the analyte is disposed proximate a two-dimensional focal area 26 and subjected to electromagnetic radiation in the manner described previously herein in relation to FIG. 3.

Figure 8:
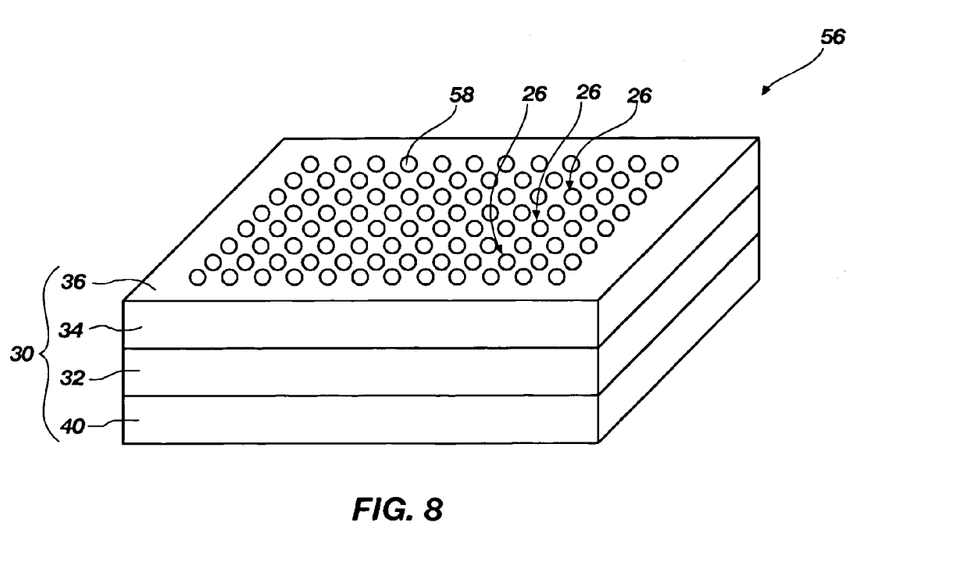
FIG. 8 is a perspective view of another exemplary Raman-enhancing structure that embodies teachings of the present invention.

FIG. 8 illustrates yet another exemplary Raman-enhancing structure 56 that embodies teachings of the present invention. The Raman-enhancing structure 56 is substantially similar to the Raman-enhancing structure 30 shown in FIG. 4. The Raman-enhancing structure 56 shown in FIG. 8, however, further includes a plurality of nanoparticles 58 formed from a Raman-enhancing material that are disposed proximate the two-dimensional focal areas 26 on the second planar surface 36 of the first layer of dielectric material 34. Only three of the two-dimensional focal areas 26 are labeled in FIG. 8. The nanoparticles 58 may be configured as, for example, nanospheres of one of Au, Ag, and Cu. Any other configuration of nanoparticle also may be used. Each two-dimensional focal area 26 may be disposed between a plurality of nanoparticles 58 comprising Raman-enhancing material. The nanoparticles 58 comprising a Raman-enhancing material may further enhance the intensity of Raman scattered radiation that is scattered by an analyte when the analyte is disposed proximate a two-dimensional focal area 26 and subjected to electromagnetic radiation in the manner described previously herein in relation to FIG. 6.

Nanoparticles, such as the nanoparticles 52 shown in FIG. 7 and the nanoparticles 58 shown in FIG. 8, may be formed on surfaces of Raman-enhancing structures by, for example, depositing a layer of Raman-enhancing material onto a surface of the Raman-enhancing structure and subsequently removing a portion of the Raman-enhancing material to leave behind the nanoparticles. Methods for depositing layers of material and subsequently selectively removing portions thereof are known in the art of microdevice and nanodevice fabrication. Alternatively, free standing nanoparticles may be formed separate from the Raman-enhancing structure and simply dispersed onto a surface of the Raman-enhancing structure when it is desired to perform Raman spectroscopy using the Raman-enhancing structure. For example, silver nanoparticles may be suspended in a fluid, which may be dispersed onto a surface of the Raman-enhancing structure. The fluid may be allowed to evaporate, leaving the nanoparticles behind on the surface of the Raman-enhancing structure, which then may be used to perform Raman spectroscopy.

Figure 9:
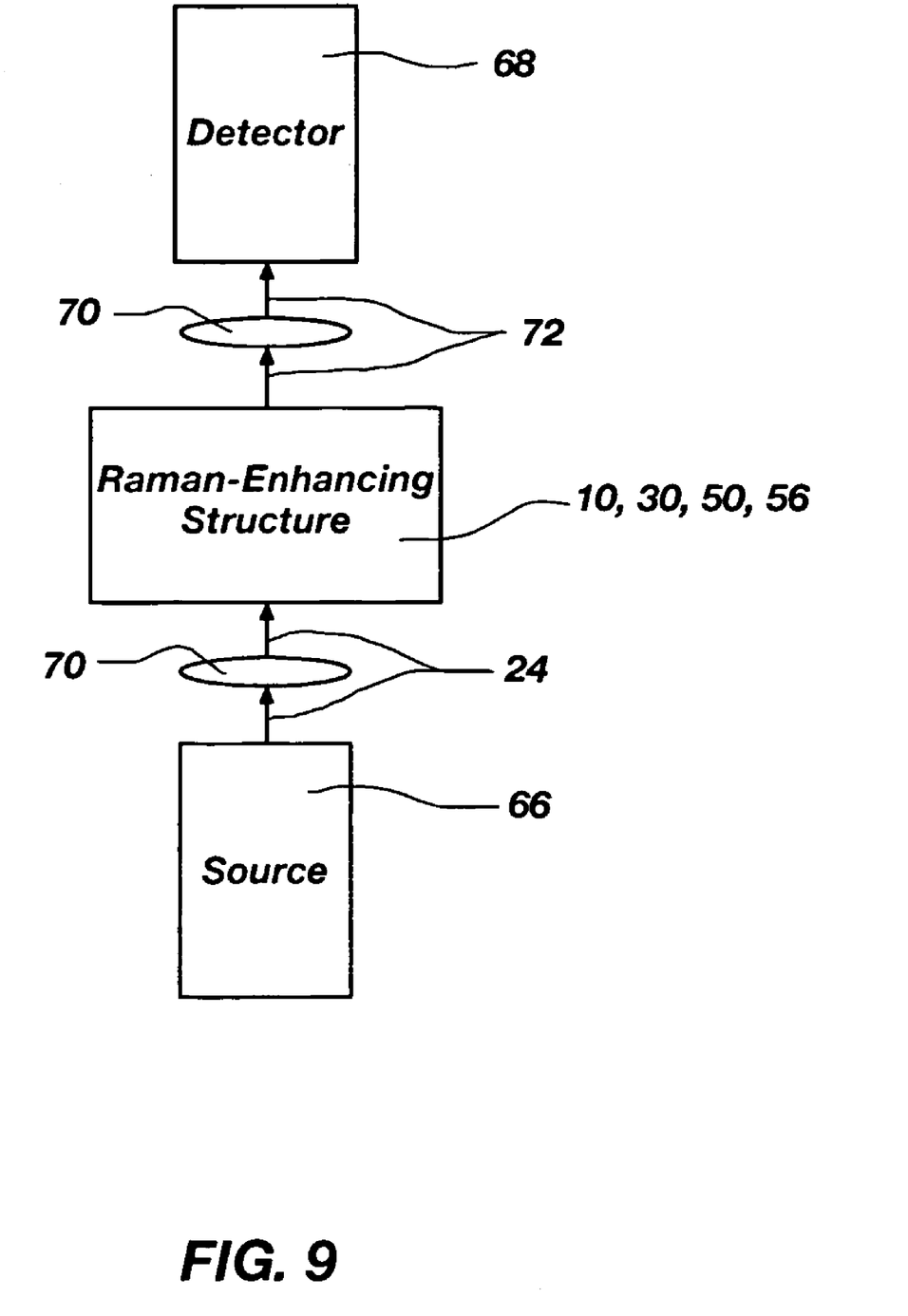
FIG. 9 is a schematic diagram of an exemplary Raman spectroscopy system that embodies teachings of the present invention.

The Raman-enhancing structure 10 shown in FIG. 1, the Raman-enhancing structure 30 shown in FIG. 4, the Raman-enhancing structure 50 shown in FIG. 7, and the Raman-enhancing structure shown in FIG. 8 each may be used to provide a Raman spectroscopy system that embodies teachings of the present invention. Such systems may be used to perform Raman spectroscopy on an analyte. A schematic diagram of an exemplary Raman spectroscopy system 64 that embodies teachings of the present invention is shown in FIG. 9. The Raman spectroscopy system 64 includes an electromagnetic radiation source 66 that is configured to emit incident electromagnetic radiation, an electromagnetic radiation detector 68 that is configured to detect Raman scattered radiation, and a Raman-enhancing structure that embodies teachings of the present invention. For example, the Raman spectroscopy system 64 may include the Raman-enhancing structure 10 shown in FIG. 1, the Raman-enhancing structure 30 shown in FIG. 4, the Raman-enhancing structure 50 shown in FIG. 7, or the Raman-enhancing structure 56 shown in FIG. 8. The Raman spectroscopy system 64 also may include various optical components 70, such as, for example, lenses and filters, positioned between the radiation source 66 and the Raman-enhancing structure, and positioned between the Raman-enhancing structure and the radiation detector 68.

The radiation source 66 may include any suitable source for emitting radiation at a desired wavelength and may be capable of emitting a tunable wavelength of radiation. The wavelengths of radiation that are emitted by the radiation source 66 may be any suitable wavelength for performing Raman spectroscopy on the analyte using the Raman-enhancing structure. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the radiation source 66.

The radiation detector 68 may be configured to receive and detect the Raman scattered radiation 72, which comprises Raman scattered photons that are scattered by an analyte disposed proximate a two-dimensional focal area of the Raman-enhancing structure. The radiation detector 68 may include a device for determining the wavelength of the Raman scattered radiation 72, such as, for example, a monochromator, and a device for determining the intensity of the Raman scattered radiation 72 such as, for example, a photomultiplier. Typically, the Raman scattered radiation 72 is scattered in all directions relative to the Raman-enhancing structure.

Optical components 70 positioned between the radiation source 66 and the Raman-enhancing structure may be used to collimate, filter, or focus the incident electromagnetic radiation 24 before the electromagnetic radiation 24 impinges on the Raman-enhancing structure. Optical components 70 positioned between the Raman-enhancing structure and the radiation detector 68 may be used to collimate, filter, or focus the Raman scattered radiation 72. For example, a filter or a plurality of filters may be employed to prevent radiation at wavelengths corresponding to the incident electromagnetic radiation 24 from impinging on the radiation detector 68, thus allowing only the Raman scattered radiation 72 to be received by the radiation detector 68.

To perform Raman spectroscopy using the Raman spectroscopy system 64, an analyte may be provided adjacent or proximate to a two-dimensional focal area 26 (FIGS. 3, 6-8) of the Raman-enhancing structure. A surface of the Raman-enhancing structure may be irradiated with incident electromagnetic radiation 24 emitted from the radiation source 66. The Raman-enhancing structure may be used to focus the electromagnetic radiation to the two-dimensional focal area 26. The analyte may be subjected to the electromagnetic radiation 24 at the two-dimensional focal area 26, and Raman scattered radiation 72 scattered by the analyte may be detected using the radiation detector 68.

While the schematic diagram of the Raman spectroscopy system 64 shown in FIG. 9 implies that the radiation source 66, the Raman-enhancing structure, and the radiation detector 68 are three distinct structures, it should be understood that the radiation source 66, the radiation detector 68, or both the radiation source 66 and the radiation detector 68 may be integrated with the Raman-enhancing structure to provide a monolithic structure.

Figure 10:
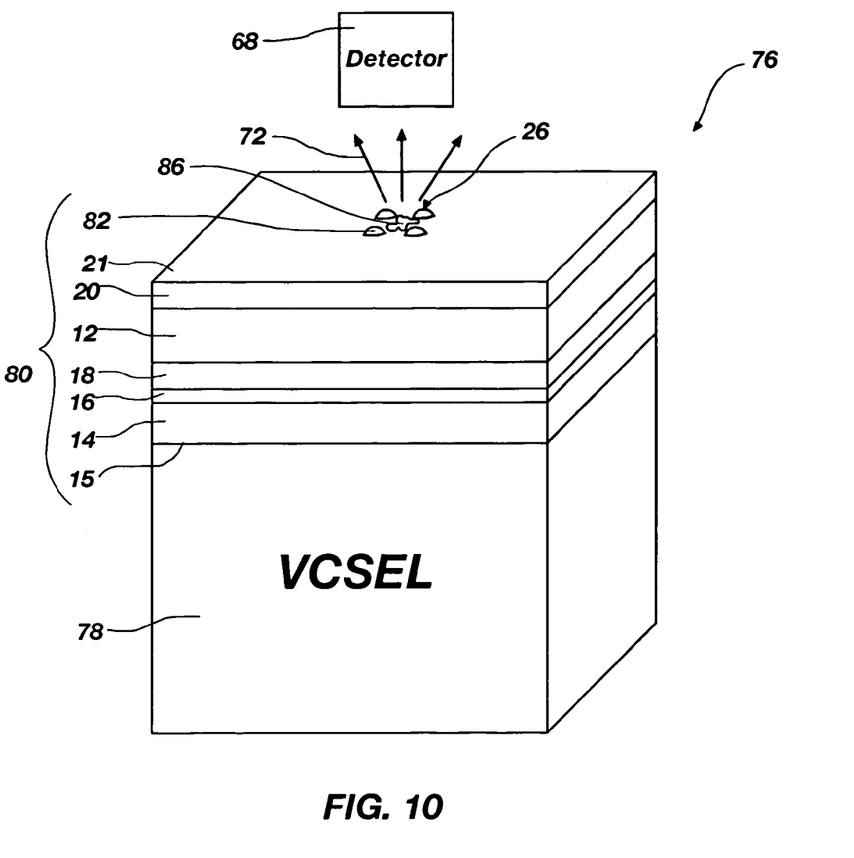
FIG. 10 is a perspective view of a Raman-enhancing structure that embodies teachings of the present invention and that is integrated with a radiation source to provide a monolithic structure that embodies teachings of the present invention.

An exemplary Raman spectroscopy system 76 that embodies teachings of the present invention is shown in FIG. 10. The Raman spectroscopy system 76 may include a vertical cavity surface emitting laser (VCSEL) 78 that is integrated with a Raman-enhancing structure 80 to form a monolithic structure. The Raman-enhancing structure 80 may be substantially similar to the Raman-enhancing structure 10 shown in FIG. 1. The Raman-enhancing structure 80, however, further includes at least two nanoparticles 82 comprising a Raman-enhancing material disposed on the exposed surface 21 of the second layer of dielectric material 20. The nanoparticles 82 may be configured, for example, as nanodots. Furthermore, the nanoparticles may be disposed proximate a two-dimensional focal area 26 of the Raman-enhancing structure 80. The Raman spectroscopy system 76 also may include a radiation detector 68 that is configured to detect Raman-scattered radiation that is scattered by an analyte 86, as described previously herein in relation to FIG. 9.

Figure 11:
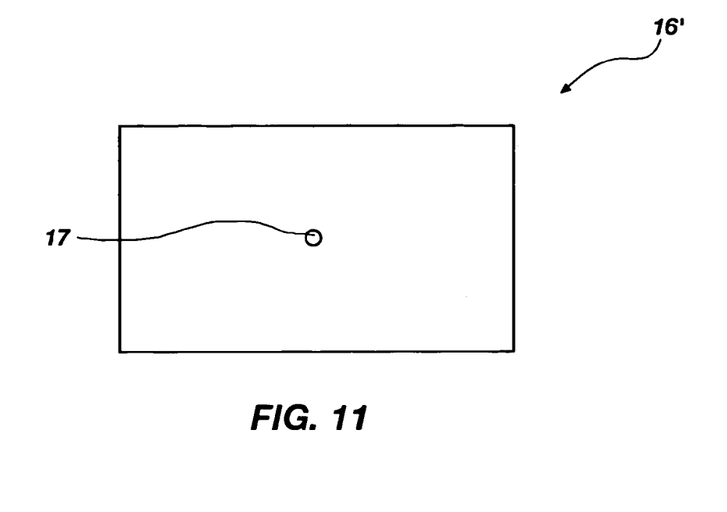
FIG. 11 is a plan view of an element of the integrated structure shown in FIG. 10.

Furthermore, the Raman-enhancing structure 80 of the Raman spectroscopy system 76 shown in FIG. 10 may include a screen layer 16', which is shown in FIG. 11. As seen therein, the screen layer 16' may include a single aperture 17 extending therethrough. The aperture 17 may have cross-sectional dimensions of less than about 100 nanometers. For example, the aperture 17 may be configured as a cylindrical hole passing through the screen layer 16' having a diameter of less than about 100 nanometers.

The VCSEL 78 may be used as an electromagnetic radiation source, and may be configured to emit incident electromagnetic radiation (not shown in FIG. 10) on the surface 15 of the first layer of dielectric material 14. An analyte 86, such as, for example, a protein, may be provided proximate the two-dimensional focal area 26 and the nanoparticles 82 on the exposed surface 21 of the second layer of dielectric material 20. Raman scattered radiation 72 scattered by the analyte 86 may be detected by the radiation detector 68. Optical components 70 (FIG. 9) optionally may be placed between the Raman-enhancing structure 80 and the radiation detector 68. The optical components may include, for example, lenses and filters for focusing the Raman scattered radiation 72 and removing any wavelengths of electromagnetic radiation corresponding to the incident electromagnetic radiation emitted by the VCSEL 78.

The Raman-enhancing structures and Raman spectroscopy systems described herein may be used to provide two-dimensional focal areas having linear dimensions less than a wavelength of incident electromagnetic radiation. As a result, these structures and systems may be used to perform Raman spectroscopy at relatively small, precise areas or regions. The structures and systems may be used to further enhance the intensity of Raman scattered radiation that is scattered by an analyte relative to currently available structures and systems. Furthermore, the Raman-enhancing structures and Raman spectroscopy systems described herein may be used to conduct hyper-Raman spectroscopy in addition to conventional Raman spectroscopy.

Although the foregoing description contains many specifics these are not to be construed as limiting the scope of the present invention, but merely as providing certain exemplary embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A Raman-enhancing structure comprising:
    a substantially planar layer of dielectric material having a first surface and a second surface, the second surface being opposite the first surface;
    a superlens configured to focus electromagnetic radiation having a wavelength greater than about 100 nanometers to a two-dimensional focal area on one of the first surface and the second surface of the layer of dielectric material, the two-dimensional focal area having linear dimensions less than about 100 nanometers; and
    at least two nanoparticles comprising a Raman-enhancing material disposed proximate the two-dimensional focal area.

2. The Raman-enhancing structure of claim 1, wherein the Raman-enhancing material comprises one of Ag, Au, and Cu.

3. The Raman-enhancing structure of claim 1, wherein each nanoparticle of the at least two nanoparticles is configured as a nanoline, a nanosphere, or a nanodot.

4. The Raman-enhancing structure of claim 1, wherein the superlens comprises a substantially planar layer of conductive material having a thickness of less than about 100 nanometers.

5. The Raman-enhancing structure of claim 4, wherein the substantially planar layer of conductive material comprises one of Ag, Au, and Cu.

6. The Raman-enhancing structure of claim 5, wherein the superlens is disposed between the substantially planar layer of dielectric material and an additional substantially planar layer of dielectric material.

7. The Raman-enhancing structure of claim 6, further comprising a screen layer, the screen layer comprising at least one aperture passing therethough having cross-sectional dimensions less than about 100 nanometers, the screen layer being disposed on a side of the superlens opposite the two-dimensional focal area.

8. The Raman-enhancing structure of claim 1, further comprising an analyte disposed proximate the two-dimensional focal area.

9. A Raman-enhancing structure comprising:
    a substantially planar layer of dielectric material having a first surface and a second surface, the second surface being opposite the first surface;
    a substantially planar layer of conductive material having a thickness of less than about 100 nanometers disposed on the first surface of the layer of dielectric material, the layer of conductive material having a plurality of apertures extending therethrough, the plurality of apertures being arranged in a two-dimensional array; and at least two nanoparticles comprising a Raman-enhancing material disposed on the second surface of the layer of dielectric material.

10. The Raman-enhancing structure of claim 9, wherein the layer of conductive material comprises Ag, Au, Al, or Cu.

11. The Raman-enhancing structure of claim 10, wherein each aperture of the plurality of apertures is substantially cylindrical, the longitudinal axis of each aperture extending in a direction substantially perpendicular to the substantially planar layer of conductive material, the plurality of apertures being arranged in a two-dimensional rectangular array, the two-dimensional rectangular array having a period defined as the distance between the longitudinal axes of adjacent apertures in the rectangular array.

12. The Raman-enhancing structure of claim 11, wherein each aperture of the plurality of apertures has a diameter of less than about 100 nanometers.

13. The Raman-enhancing structure of claim 12, wherein the rectangular array of apertures has a period in a range from about 30 nanometers to about 1 micron.

14. A method for performing Raman spectroscopy comprising:
   generating electromagnetic radiation having a selected wavelength greater than about 100 nanometers;
   focusing at least a portion of the electromagnetic radiation via a superlens to a two-dimensional focal area having linear dimensions less than about 100 nanometers;
   providing an analyte proximate the two-dimensional focal area;
   subjecting the analyte to the focused electromagnetic radiation; and
   detecting Raman scattered radiation scattered by the analyte.

15. The method for performing Raman spectroscopy of claim 14, wherein providing a superlens comprises providing a thin layer of Ag, Au, or Cu.

16. A method for performing Raman spectroscopy comprising:
   generating electromagnetic radiation having a selected wavelength greater than about 100 nanometers;
   focusing at least a portion of the electromagnetic radiation to a two-dimensional focal area having linear dimensions less than about 100 nanometers, comprising:
      providing a substantially planar layer of conductive material having a thickness of less than about 100 nanometers, the layer of conductive material having a plurality of apertures extending therethrough, the plurality of apertures being arranged in a two-dimensional array;
      irradiating a surface of the layer of conductive material with the electromagnetic radiation; and
      exciting surface plasmons on a surface of the layer of conductive material;
   providing an analyte proximate the two-dimensional focal area;
   subjecting the analyte to the focused electromagnetic radiation; and
   detecting Raman scattered radiation scattered by the analyte.

17. The method for performing Raman spectroscopy of claim 16, wherein providing a substantially planar layer of conductive material comprises providing a layer of Ag, Au, or Cu.

18. The method for performing Raman spectroscopy of claim 16, wherein each aperture of the plurality of apertures is substantially cylindrical, the longitudinal axis of each aperture extending in a direction substantially perpendicular to the substantially planar layer of conductive material, the plurality of apertures being arranged in a two-dimensional rectangular array, the two-dimensional rectangular array having a period defined as the distance between the longitudinal axes of adjacent apertures in the rectangular array.

19. The method for performing Raman spectroscopy of claim 18, wherein the substantially planar layer of conductive material has a thickness in a range from about 20 nanometers to about 100 nanometers.

20. The method for performing Raman spectroscopy of claim 19, wherein each aperture of the plurality of apertures has a diameter of less than about 100 nanometers, and wherein the rectangular array of apertures has a period in a range from about 30 nanometers to about 1 micron.

21. The method for performing Raman spectroscopy of claim 14, wherein detecting Raman scattered radiation scattered by the analyte comprises detecting at least one higher order harmonic mode of Raman scattered radiation.

\* \* \* \* \*

UNITED STATES PATENT AND TRADEMARK OFFICE
CERTIFICATE OF CORRECTION

PATENT NO. : 7,474,397 B2  Page 1 of 1
APPLICATION NO. : 11/413377
DATED : January 6, 2009
INVENTOR(S) : Shih-Yuan Wang et al.

It is certified that error appears in the above-identified patent and that said Letters Patent is hereby corrected as shown below:

In column 12, line 51, in Claim 7, delete "therethough" and insert -- therethrough --, therefor.

Signed and Sealed this

Twenty-first Day of July, 2009

JOHN DOLL
*Acting Director of the United States Patent and Trademark Office*